(12) United States Patent
Tolmie et al.

(10) Patent No.: US 10,426,913 B2
(45) Date of Patent: *Oct. 1, 2019

(54) APPARATUS AND METHOD FOR MONITORING NITRIC OXIDE DELIVERY

(71) Applicant: Mallinckrodt Hospital Products IP Limited, Dublin (IE)

(72) Inventors: Craig R. Tolmie, Stoughton, WI (US); Robert Schnitman, Colchester, CT (US); Joseph J. Medicis, Syracuse, NY (US); Jim Potenziano, Binghamton, NY (US); Jaron Acker, New York, NY (US); Jeffrey Schmidt, Oregon, WI (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 29 days.

This patent is subject to a terminal disclaimer.

(21) Appl. No.: 13/800,287

(22) Filed: Mar. 13, 2013

(65) Prior Publication Data

US 2013/0192595 A1   Aug. 1, 2013

Related U.S. Application Data

(63) Continuation-in-part of application No. 13/671,057, filed on Nov. 7, 2012, now Pat. No. 9,770,570.
(Continued)

(51) Int. Cl.
*A61M 16/00* (2006.01)
*A61M 16/12* (2006.01)
(Continued)

(52) U.S. Cl.
CPC ........ *A61M 16/12* (2013.01); *A61M 16/0051* (2013.01); *A61M 16/024* (2017.08);
(Continued)

(58) Field of Classification Search
CPC .......... A61M 16/0051; A61M 16/0057; A61M 16/0666; A61M 16/085; A61M 16/104;
(Continued)

(56) References Cited

U.S. PATENT DOCUMENTS 5,558,083 A   9/1996   Bathe et al.
5,692,497 A   12/1997   Schnitzer et al.
(Continued)

FOREIGN PATENT DOCUMENTS

EP   2968824 B1   1/2019
JP   H110509062   9/1998
(Continued)

OTHER PUBLICATIONS

PCT International Search Report and Written Opinion in PCT/US2014/025442, dated Jul. 16, 2014, 15 pages.
(Continued)

*Primary Examiner* — Tan-Uyen T Ho
*Assistant Examiner* — Victoria Murphy

(57) ABSTRACT

Described is an apparatus for monitoring nitric oxide delivery, wherein such apparatus comprises a display that provides a visual and/or numeric indication of the calculated dose of nitric oxide. Also described is a method of monitoring nitric oxide delivery, wherein the breathing gas flow rate and therapeutic gas flow rate are measured and used to determine the calculated dose of nitric oxide, which is then displayed. In some embodiments, an alert is provided when the calculated dose rises above or falls below a predetermined level or range.

19 Claims, 7 Drawing Sheets

Related U.S. Application Data

(60) Provisional application No. 61/556,525, filed on Nov. 7, 2011.

(51) Int. Cl.
    *A61M 16/06* (2006.01)
    *A61M 16/10* (2006.01)
    *A61M 16/08* (2006.01)

(52) U.S. Cl.
    CPC ....... *A61M 16/0666* (2013.01); *A61M 16/085* (2014.02); *A61M 2016/0039* (2013.01); *A61M 2016/102* (2013.01); *A61M 2202/0275* (2013.01); *A61M 2205/16* (2013.01); *A61M 2205/18* (2013.01); *A61M 2205/3334* (2013.01); *A61M 2205/502* (2013.01); *A61M 2205/581* (2013.01); *A61M 2205/583* (2013.01)

(58) Field of Classification Search
    CPC .......... A61M 16/12; A61M 2016/0039; A61M 2016/102; A61M 2202/0275; A61M 2205/16; A61M 2205/18; A61M 2205/3334; A61M 2205/502; A61M 2205/581
    See application file for complete search history.

(56) References Cited

U.S. PATENT DOCUMENTS

| | | | |
|---|---|---|---|
| 5,732,693 | A | 3/1998 | Bathe et al. |
| 5,752,504 | A | 5/1998 | Bathe |
| 5,842,468 | A * | 12/1998 | Denyer ............. A61M 15/0086 128/200.14 |
| 5,842,486 | A | 12/1998 | Davis et al. |
| 5,881,723 | A | 3/1999 | Wallace et al. |
| 5,890,490 | A | 4/1999 | Aylsworth et al. |
| 5,918,596 | A | 7/1999 | Heinonen |
| 6,158,434 | A | 12/2000 | Lugtigheid et al. |
| 6,164,276 | A | 12/2000 | Bathe et al. |
| 6,581,599 | B1 | 6/2003 | Stenzler et al. |
| 7,201,166 | B2 | 4/2007 | Blaise et al. |
| 7,455,062 | B2 | 11/2008 | Roehl et al. |
| 7,523,752 | B2 * | 4/2009 | Montgomery .... A61M 16/0051 128/204.18 |
| 2005/0076906 | A1 | 4/2005 | Johnson |
| 2005/0172966 | A1* | 8/2005 | Blaise ................... A61M 16/12 128/204.21 |
| 2007/0062527 | A1 | 3/2007 | Montgomery et al. |
| 2007/0181126 | A1 | 8/2007 | Tolmie et al. |
| 2009/0090363 | A1 | 4/2009 | Niland et al. |
| 2011/0154241 | A1 | 6/2011 | Skidmore et al. |
| 2012/0199123 | A1 | 8/2012 | Stenzler et al. |
| 2013/0192595 | A1 | 8/2013 | Tolmie et al. |

FOREIGN PATENT DOCUMENTS

| | | |
|---|---|---|
| JP | 2001-521416 | 11/2001 |
| JP | 2002-315793 | 10/2002 |
| JP | 2003511143 | 3/2003 |
| JP | 2004-524933 | 8/2004 |
| JP | 2004-167284 | 12/2004 |
| JP | 2006317243 | 11/2006 |
| JP | 2009508637 | 3/2009 |
| JP | 2011-502547 | 1/2011 |
| WO | 199841267 A1 | 9/1998 |

OTHER PUBLICATIONS

PCT International Preliminary Report on Patentability and Written Opinion in PCT/US2012/063883, dated May 22, 2014, 8 pages.
"International Search Report and Written Opinion of PCT/US2012/063883", dated Feb. 18, 2013, 12 pages.
PCT International Preliminary Report on Patentability in PCT/US2014/025442, dated Sep. 24, 2015, 10 pages.
Final Rejection related to Japanese Application 2014-540210 dated Jun. 16, 2017, 7 pages.
European Communication related to European Application 12791615.3 dated Jul. 28, 2017, 8 pages.
Dffice action related to Australian Application 2014244334 dated Jul. 18, 2017, 4 pages.
Google translated Abastract Only related to Japanese Application JPH09 75459, 1 page.
Notice of Reasons for Rejection regarding Japanese Patent Application No. 2016-501851 dated Nov. 14, 2017, 5 pages.
Decision of Rejection regarding Japanese Patent Application No. 2016-501851 dated Mar. 27, 2018, 2 pages.
Dube, I. et al, Comparison of two administration techniques of inhaled nitric oxide on nitrogen dioxide production, Canadian Journal of Anaesthesia, 1995, Vol. 42, No. 10, pp. 922-927.
Office Action related to Canadian Patent Application 2,854,776, dated Aug. 31, 2018, 6 pages.
Office Action related to Mexican Patent Application MX/a/2014/005524 issued Nov. 3, 2017, 5 pages.
European Search Report related to 17199979.0 dated Mar. 18, 2018, 9 pages.
Office Action related to Mexican Patent Application MX/a/2014/005524 issued Apr. 25, 2017, 7 pages.
INOmax DS (Delivery System): Operation Manual (800 ppm INOMAX (nitric oxide) for Inhalation), Ikaria, Inc. 2010, 112 pages.
INOmax DSIR (Delivery System): Operation Manual (800 ppm INOMAX (nitric oxide) for Inhalation), Ikaria, Inc. 2012, 136 pages.
INOmax Label, Nitric Oxide Gas, INO Therapeutics 2013, 2 pages.
INOvent Delivery System: Operation and Maintenance Manual (CGA Variant), Datex-Ohmeda, Inc. 2000, 180 pages.
International Search Report and Written Opinion of PCT/US2012/063883, dated Feb. 8, 2013, 10 pages.
Using the INOpulse DS Subject Guide, Ikaria, Inc. 2012, 50 pages.
International Search Report and Written Opinion of PCT/US2014/025442, dated Jul. 8, 2014, 14 pages.
Office Action related to Japanese Patent Application 2017-206969 dated Nov. 6, 2018, 10 pages.
Office Action related to Australian Patent Application 2018204804 dated Jan. 25, 2019, 4 pages.
Office action related to Australian Application 2014244334 dated Jan. 10, 2018, 4 pages.
Office action related to Australian Application 2014244334 dated May 21, 2018, 5 pages.
Office action related to Mexican Patent Application MX/a/2015/012179 dated Oct. 2, 2018, 3 pages.
Office Action related to U.S. Appl. No. 131671,057, dated Sep. 1, 2016, 17 pages.
Office Action related to U.S. Appl. No. 131671,057, dated Feb. 8, 2017, 18 pages.
Office Action related to Mexican Patent Application MX/a/2014/005524 dated Feb. 21, 2018, 4 pages.

* cited by examiner

APPARATUS AND METHOD FOR MONITORING NITRIC OXIDE DELIVERY

CROSS-REFERENCE TO RELATED APPLICATIONS

This application is a continuation-in-part under 35 U.S.C. § 120 of U.S. patent application Ser. No. 13/671,057, filed Nov. 7, 2012, which claims the benefit under 35 U.S.C. § 119(e) to U.S. Provisional Application No. 61/556,525, filed Nov. 7, 2011, the entire contents of which are incorporated herein by reference in their entirety.

TECHNICAL FIELD

Embodiments of the present invention generally relate to the field of apparatuses and methods for nitric oxide delivery.

BACKGROUND

Nitric oxide (NO) is a gas that, when inhaled, acts to dilate blood vessels in the lungs, improving oxygenation of the blood and reducing pulmonary hypertension. Because of this, nitric oxide is provided in inspiratory breathing gases for patients with pulmonary hypertension.

Often, apparatuses used for nitric oxide drug delivery provide a direct ppm dose setting based on patient inspired breathing gas in order to provide a constant concentration within the breath period. As the flow rate of breathing gas rapidly rises and falls within the inspiratory or expiratory phases, it becomes difficult to provide a proportional ratio-metric dose of delivered NO gas dependent on inspired flow.

Methods of closed loop proportional flow control which are utilized to titrate the desired dose have limitations regarding dynamic range and impulse step response to changes in breathing gas flow. The primary limitation is known to be at the extremes of the NO flow control range, i.e. lower than 1% or greater than 100% of the NO flow control range. Typical flow control technologies including electromagnetic valve in combination with flow sensor and microprocessor running PID (proportional, integral, derivative) control are utilized for wild stream blending of gases. On the lower 1% end of the control range, integral error is minimal to drive sufficient control system proportional valve gain. An over-damped system, combined with poor flow control valve step response can under-deliver the desired NO gas for a significant portion of the breath period. At the opposite extreme, when peak inspired flows exceed 100% of the NO flow control range for a significant portion of the breath period, there is also under-delivery of the set dose. Additionally, a highly tuned, proportional control, fast response control system combined with a large hysteresis, or a poorly acting proportional control valve can act to over-deliver the desired dose when operating in the lower 1% of the control range.

In fact, some delivery apparatuses shut down automatically when the calculated ratio-metric amount of NO flow from the inspired gas flow is found to be greater than 2 times or less than one half of the desired ppm set dose. When supply of nitric oxide is abruptly cut off, patients may experience adverse effects such as worsening of partial pressure of oxygen in arterial blood ($PaO_2$) and increasing pulmonary artery pressure (PAP).

Variability or irregularity in an unknown inspired flow profile from a support device such as a breathing gas delivery system may produce such flow conditions, and when combined with insufficient dynamic proportional control range, may then result in shutdown of the inhaled NO delivery system or other NO delivery apparatus. Additionally, current inhaled NO delivery systems have insufficient dynamic delivery range and cannot be used with gentle ventilation as gentle ventilation often requires lower flows than conventional ventilation. This can, again, result in shutdown of the delivery apparatus with resulting rebound hypertension and oxygen desaturation, which may result in adverse events as serious as death.

In addition, nitric oxide delivery system architecture provides complete independence of NO gas delivery from gas concentration measurement within the inspired limb of the patient circuit. Traditionally, gas concentration measurements are displayed in ppm on the main screen of the device with NO proportional delivery control performance suppressed. With this independence, when NO set dose is not equal to the reported concentration measurement, the user has difficulty in assessing which portion of the system monitoring or delivery is performing poorly.

Therefore, there is a need to monitor and display the flow(s) from the patient support device to provide safe delivery of nitric oxide, as well as a need to provide the user a method of determining limitations of dynamic ratio-metric gas NO delivery blending performance.

SUMMARY OF THE INVENTION

A first aspect of the invention relates to an apparatus to deliver therapeutic gas to a patient. According to one or more embodiments, the apparatus comprises a first inlet to be placed in fluid communication with a therapeutic gas supply comprising nitric oxide, a second inlet to be placed in fluid communication with a breathing gas delivery system that provides a breathing gas to the patient, a therapeutic gas injector module to be placed in fluid communication with the first inlet and the second inlet to provide a combined flow of breathing gas and therapeutic gas, an outlet in fluid communication with the therapeutic injector module to supply the combined flow of breathing gas and therapeutic gas to a patient, and a control circuit including a first flow sensor to measure the flow of breathing gas from the breathing gas delivery system and a second flow sensor to measure flow of therapeutic gas, wherein the control circuit determines a calculated dose of nitric oxide based on the measured flow of breathing gas and the measured flow of therapeutic gas or a known flow of therapeutic gas, and a display in communication with the control circuit that provides a visual and/or numeric indication of the calculated dose of nitric oxide and an indicator to inform a user of the apparatus when the flow of breathing gas rises above or falls below a predetermined level.

In one or more embodiments of this aspect, the control circuit includes a CPU and a flow controller, wherein the CPU sends and receives signals to the flow sensor and the flow controller such that the control circuit delivers a proportional flow of therapeutic gas to provide a desired concentration of nitric oxide to the patient. In certain embodiments, the control circuit further comprises clinical decision support software. In a particular embodiment, the clinical decision support software comprises instructions to reset any upper and lower limits of maximum and minimum calculated dose to avert shutdown of the apparatus.

In one or more embodiments, the visual and/or numeric indication of the calculated dose of nitric oxide is provided in parts per million (ppm) and/or as a percentage of a desired delivery concentration. In some embodiments, the calculated dose of nitric oxide is one or more of an average calculated dose, an instantaneous calculated dose, a maximum calculated dose and a minimum calculated dose.

In certain embodiments, the apparatus further comprises an indicator that provides an alert when the calculated dose of nitric oxide rises above or falls below a predetermined level. According to one or more embodiments, the alert includes one or more of an audible alert, a visual alert and a text alert. In some embodiments, the indicator is an icon or graphic on the display that provides a visual and/or numeric indication of the calculated dose.

One or more embodiments of this aspect provide that the display also provides a visual and/or numeric indication of the volumetric flow of breathing gas. In certain embodiments, the visual and/or numeric indication includes one or more of volumetric flow rate, tidal volume, and minute ventilation.

According to one or more embodiments, the breathing gas delivery system comprises a ventilation apparatus.

Another aspect of the invention relates to a method of monitoring the delivery of therapeutic gas to a patient comprising: providing a flow of breathing gas, providing a flow of therapeutic gas comprising nitric oxide, measuring the flow of breathing gas to obtain a measured flow of breathing gas, measuring the flow of therapeutic gas comprising nitric oxide to obtain a measured flow of therapeutic gas or obtaining a known flow of therapeutic gas, delivering the breathing gas and therapeutic gas to a patient, determining a calculated dose of nitric oxide based on the measured flow of breathing gas and the measured flow of therapeutic gas or the known flow of therapeutic gas, and displaying the calculated dose of nitric oxide and/or measured flow of breathing gas on a display module.

According to one or more embodiments, the method further comprises comparing the calculated dose of nitric oxide to a predetermined limit and providing an alert if the calculated dose of nitric oxide is above or below the limit. In certain embodiments, the alert includes one or more of an audible alert, a visual alert and a text alert.

In some embodiments, the predetermined limit comprises a delivery error greater than or equal to about 25%. Other predetermined limits include, but are not limited to, delivery errors greater than or equal to the following values: +/−1%, +/−2%, +/−5%, +/−10%, +/−15%, +/−20%, +/−25%, +/−30%, +/−35%, +/−40%, +/−45%, +/−50%, +/−55%, +/−60%, +/−65%, +/−70%, +/−75%, +/−80%, +/−85%, +/−90%, +/−95% or +/−100%.

According to one or more embodiments, the calculated dose of nitric oxide is displayed in parts per million (ppm) and/or as a percentage of a desired delivery concentration. In some embodiments, the calculated dose of nitric oxide is one or more of an average calculated dose, an instantaneous calculated dose, a maximum calculated dose and a minimum calculated dose.

In certain embodiments, the method further comprises adjusting the flow of breathing gas delivered to the patient and/or the desired target NO concentration in response to the alert. For example, the flow of breathing gas may be adjusted by having a clinician change a setting on the ventilator.

In some embodiments, the method further comprises displaying the measured flow of breathing gas. In one or more embodiments, displaying the measured flow of breathing gas includes displaying one or more of volumetric flow rate, tidal volume, and minute ventilation. Some embodiments provide that the measured flow of breathing gas is one or more of an average flow rate, an instantaneous flow rate, a peak flow rate and a minimum measured flow rate.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
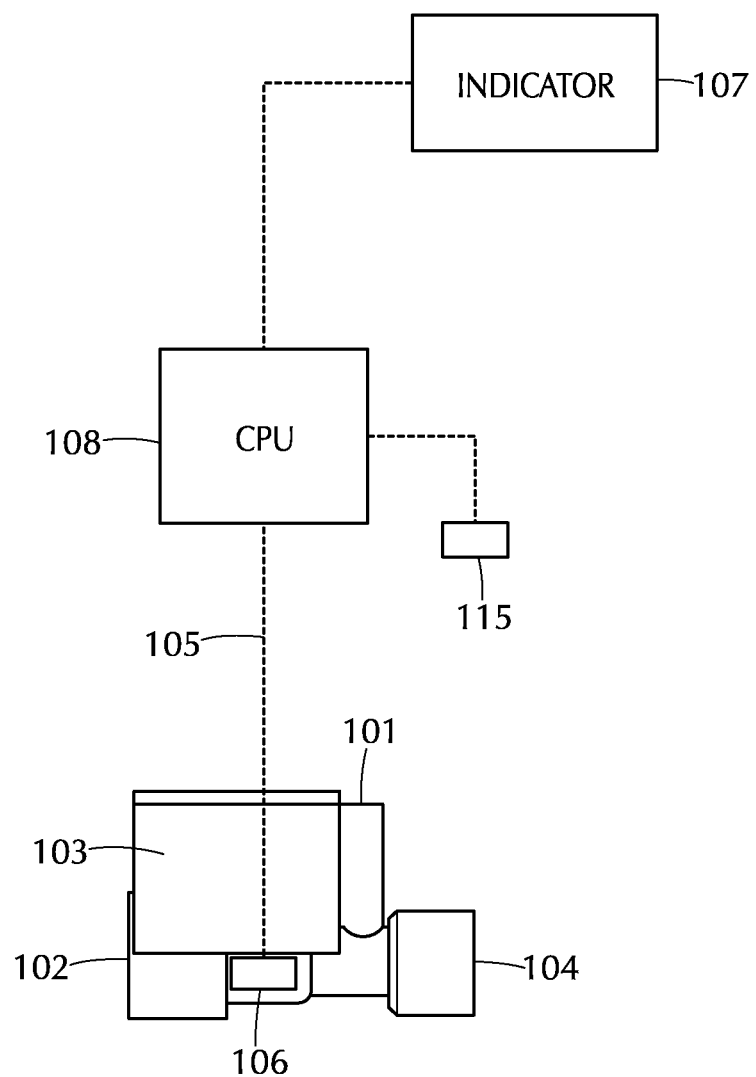
FIG. 1 depicts an apparatus for monitoring patient inspired gas flow containing a therapeutic gas to a patient in accordance with one or more embodiments of the invention.

Before describing several exemplary embodiments of the invention, it is to be understood that the invention is not limited to the details of construction or process steps set forth in the following description. The invention is capable of other embodiments and of being practiced or being carried out in various ways.

Certain embodiments of the invention generally provide an apparatus for delivering a therapeutic gas comprising nitric oxide to a patient. The therapeutic gas comprises nitric oxide in a carrier gas such as nitrogen. Suitable therapeutic gases can have varying concentrations of nitric oxide, and exemplary concentrations of nitric oxide in the therapeutic gas include, but are not limited to, 100 ppm to 10,000 ppm. In a particular embodiment, the concentration of nitric oxide is about 800 ppm.

The apparatus includes a control circuit and a display that measures the flow of therapeutic gas and breathing gas to determine and display a calculated dose of nitric oxide.

Other embodiments pertain to a method of monitoring the delivery of therapeutic gas comprising nitric oxide to a patient.

In one aspect, provided are apparatuses that comprise: a first inlet for receiving a therapeutic gas supply comprising nitric oxide; a second inlet for receiving a breathing gas; a therapeutic gas injector module in fluid communication with the first inlet and the second inlet to provide a combined flow of therapeutic gas and breathing gas; an outlet in fluid communication with the therapeutic gas injector module for supplying the breathing gas and therapeutic gas to a patient; and a control circuit to determine a calculated dose of nitric oxide based on the measured flow of breathing gas and the measured flow of therapeutic gas or a known flow of therapeutic gas.

One or more embodiments relate to an apparatus comprising: a first inlet to be placed in fluid communication with a therapeutic gas supply comprising nitric oxide; a second inlet to be placed in fluid communication with a breathing gas delivery system that provides a breathing gas to the patient; a therapeutic gas injector module in fluid communication with the first inlet and the second inlet to provide a combined flow of therapeutic gas and breathing gas; an outlet in fluid communication with the therapeutic gas injector module and configured to supply breathing gas and therapeutic gas to a patient; a control circuit including a first flow sensor to measure the flow of breathing gas from the breathing gas delivery system and a second flow sensor to measure flow of therapeutic gas, wherein the control circuit determines a calculated dose of nitric oxide based on the measured flow of breathing gas and the measured flow of therapeutic gas; and a display in communication with the control circuit that provides a visual and/or numeric indication of the calculated dose of nitric oxide. Alternatively, instead of determining a calculated dose of nitric oxide based on a measured flow of therapeutic gas, the calculated dose may be based on a known or assumed flow of therapeutic gas. This known flow of therapeutic gas may be a constant flow of therapeutic gas, such as if the nitric oxide delivery apparatus is in a backup mode.

FIG. 1 illustrates one embodiment of an apparatus for monitoring delivery of a therapeutic gas in accordance with this aspect. First inlet 101 is configured to be placed in fluid communication with a therapeutic gas comprising nitric oxide. Second inlet 102 is configured to be placed in fluid communication with a breathing gas delivery system that provides a breathing gas to a patient. Therapeutic injector module 103 is in fluid communication with first inlet 101 and second inlet 102, as well as outlet 104. The side view of therapeutic injector module 103 is shown. Outlet 104 is in fluid communication with first inlet 101 and second inlet 102, and is configured to supply breathing gas and therapeutic gas to a patient. A first flow sensor 106 is in fluid communication and downstream of second inlet 102, and monitors the flow of breathing gas through therapeutic injector module 103. Control circuit 105 is in communication with therapeutic injector module 103, and connects flow sensor 106 to CPU 108 and indicator 107. Control circuit 105 may also be in communication with a second flow sensor 115 that measures the flow of therapeutic gas into the therapeutic injector module 103. When the flow rate as measured by flow sensor 106 is above or below a predetermined level, central processing unit (CPU) 108 may send a signal to indicator 107. The CPU 108 may also determine a calculated dose of nitric oxide based on the measured flow rate of therapeutic gas from flow sensor 115, the measured flow rate of breathing gas from flow sensor 106, and the concentration of nitric oxide in the therapeutic gas. Alternatively, the CPU 108 may use a known flow rate of therapeutic gas to determine the calculated dose. Indicator 107 can inform a user of the apparatus that the flow is outside of a particular range. The indicator 107 may be part of a display, such as an icon or graphic on a display screen.

Flow sensors 106 and 115 can be any appropriate flow measuring device. This includes, but is not limited to, a pneumotach, hot wire anemometer, thermal flow sensor, variable orifice, thermal time-of-flight, rotating vane and the like. Also suitable are flow transducers that measure pressure, such as a pressure drop though an orifice, in order to determine flow. According to one embodiment, the flow sensor 106 is part of the therapeutic injector module 103. In one such embodiment, the flow sensor 106 comprises a hot film sensor and a thermistor. The thermistor measures the temperature of the breathing gas flowing through the injector module 103. The constant temperature hot film sensor measures the flow of breathing gas in proportion to the energy required to maintain the platinum film temperature constant. In other embodiments, the flow sensor 106 is upstream of the therapeutic injector module 103.

In some embodiments, flow sensor 115 is part of the therapeutic injector module. In other embodiments, flow sensor 115 is upstream of the therapeutic injector module 103, such as in the control module of the nitric oxide delivery device.

The term "control circuit" is intended to encompass a variety of ways that may be utilized to carry out various signal processing functions to operate the therapeutic gas delivery apparatus. In a particular embodiment, the control circuit includes a CPU 108 and a flow controller. The CPU 108 can send and receive signals to the flow sensor 103 and the flow controller (not shown) such that the control circuit maintains set NO dose of therapeutic gas to the patient. In a specific embodiment, the CPU obtains information from the flow sensor and from an input device that allows the user to select the desired dose of nitric oxide.

In a specific embodiment of a control circuit, the flow sensor 103 is in communication with a CPU 108 that monitors the flow of each of the gases to patient as described herein. If a specific dose of nitric oxide is to be administered, the CPU 108 can calculate the necessary flow of therapeutic gas based on the measured flow of breathing gas and the concentration of nitric oxide in the therapeutic gas. Such a calculation can be performed using the following equation:

$$Q_{therapeutic} = [\gamma_{set}/(\gamma_{therapeutic} - \gamma_{set})] * Q_{breathing}$$

wherein $Q_{breathing}$ is the flow rate of breathing gas, $\gamma_{set}$ is the desired nitric oxide concentration, $\gamma_{therapeutic}$ is the concentration of nitric oxide in the therapeutic gas supply, and $Q_{therapeutic}$ is the necessary flow of therapeutic gas to provide the desired concentration of nitric oxide in the gas mixture.

The central processing unit may be one of any forms of a computer processor that can be used in an industrial or medical setting for controlling various medical gas flow devices and sub-processors. The CPU can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to the CPU to support the CPU in a conventional manner. These circuits include cache, power supplies, clock circuits, input/output circuitry, subsystems, and the like.

The control circuit may further comprise clinical decision support software. Such software may provide instructions for a variety of tasks, such as providing alerts when the calculated dose of NO and/or the measured flow of breathing gas rises above or falls below a predetermined level. The predetermined level may be the level at which the apparatus shuts down. Alternatively, the predetermined level may be a level that is reached prior to apparatus shutdown. Thus, for an apparatus that shuts down when the delivered NO dose is below a minimum threshold, the predetermined level may be above this minimum threshold.

The predetermined level may be built into the clinical decision support software, or it may be provided by the user through an input device. In one embodiment, the clinical decision support software comprises instructions to reset the upper and lower limits of maximum and minimum concentrations, dose errors or flows at which a shutdown is triggered. According to certain embodiments, the clinical decision software comprises instructions to provide an alert when these limits are reached and avert the potential for shutdown of the apparatus, which would lead to the lack of drug delivery. Alternatively, the apparatus may comprise clinical decision software that provides instructions such that the apparatus may automatically adjust these limits without the need for user intervention.

The clinical decision software may also include instructions to alter the time sensitivity of the apparatus to changes in breathing gas flow and/or calculated dose. As a result, the apparatus may change the time period necessary for a sustained low flow condition or under-delivery condition before the apparatus shuts down. For example, the apparatus can increase the time before shutdown from about 1 to 2 seconds to several seconds, so that a shutdown will only occur if the low flow and/or under-delivery is sustained for a longer period of time.

The apparatus may also comprise an indicator to inform a user of the apparatus when the calculated dose and/or flow of breathing gas rises above or falls below a predetermined level. In one or more embodiments, the indicator provides an alert when the calculated dose and/or flow of breathing gas rises above or falls below the predetermined level. In certain embodiments, the alert includes one or more of an audible alert, a visual alert and a text alert. Such alerts can be provided at the location of the apparatus itself, or may be provided at a remote location, such as directly to the medical staff or to a nursing station. When the alert is provided to a remote location, the signal may be transferred from the apparatus to the remote location by any wired or wireless communication. Examples of alerts include text messages, sirens, sounds, alarms, flashing images, changes in display color, or any other means of attracting the attention of a user.

In certain embodiments, more than one alert may be provided. For example, a low priority alert may be provided when the flow of breathing gas falls below a first predetermined level, and a high priority alert may be provided when the flow of breathing gas falls below a second, lower predetermined level. Such a tiered alert system can put medical staff on notice of a relatively small deviation in flow rate, but also provide a more serious alert when a dangerous condition exists that requires immediate attention. Alternatively, a high priority alert can be provided when the flow rate is below the predetermined level for a certain period of time, thus indicating a sustained low flow condition.

The apparatus can also include a display that provides a visual and/or numeric indication of the volumetric flow of breathing gas and/or the calculated dose. This visual and/or numeric indication can include any means of displaying the flow of breathing gas and/or calculated dose, including numerals, graphics, images or the like. The display can also be any sort of appropriate display device, including a dial, gauge or other analog device, or any electronic display device, including an LED, LCD, CRT, etc. Such device need not necessarily be connected to the apparatus and may be utilized in a remote capacity. In certain embodiments, the visual and/or numeric indication of the breathing gas flow includes one or more of volumetric flow rate, tidal volume, and minute ventilation. The displayed flow rate may include one or more of the following: average flow rate, instantaneous flow rate, peak flow rate, minimum measured flow rate, or other like measurements relating to the breathing gas flow.

Figure 5:
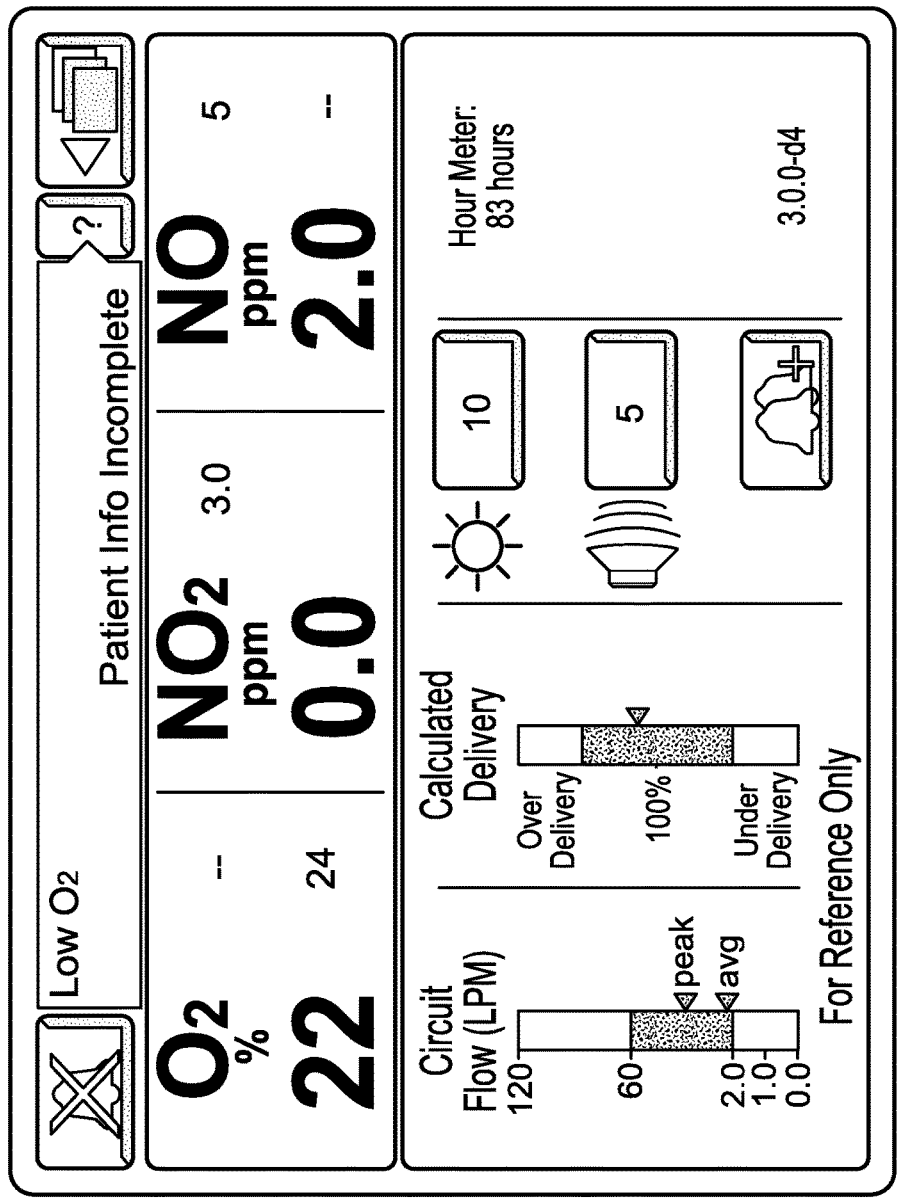
FIG. 5 depicts a screen displaying the flow of breathing and calculated NO dose delivered compared to set dose over a reporting time period of measured breathing gas flow rate gas in accordance with one or more embodiments of the invention.

An exemplary screen displaying the flow of breathing gas is shown in FIG. 5. The screen in FIG. 5 has an indicator in the bottom left corner showing the average and peak flow rates of breathing gas. In FIG. 5, the indicator has a range of 0.0 to 120 standard liters per minute. The black region from 2.0 to 60 liters per minute is the target range for the breathing gas, with 60 liters per minute as a high flow limit and 2.0 liters per minute as a low flow limit. The white regions above 60 liters per minute and below 2.0 liters per minute may be regions where delivery accuracy may differ from expected, when the set dose is above 40 ppm, or where which an alarm is emitted or other notification is given to the user such that the user is informed to make an appropriate correction to the respiratory device or the NO delivery system. The low flow and high flow limits may be adjusted depending on the sensitivity of the flow sensor and/or injector module, or depending on the patient to be treated. As can be seen from FIG. 5, the screen may also display other information, such as the $O_2$, $NO_2$ and NO concentrations that are administered to the patient. In addition, the screen shown in FIG. 5 may also display other parameters relating to the breathing gas flow and nitric oxide delivery, such as the instantaneous breathing gas flow rate, minimum measured breathing gas flow rate, average nitric oxide dose rate, instantaneous nitric oxide dose rate, minimum and maximum nitric oxide dose rates, average nitric oxide flow rate, instantaneous nitric oxide flow rate, minimum and maximum nitric oxide flow rates, target nitric oxide delivery concentration, cylinder nitric oxide concentration, etc.

Figure 7:
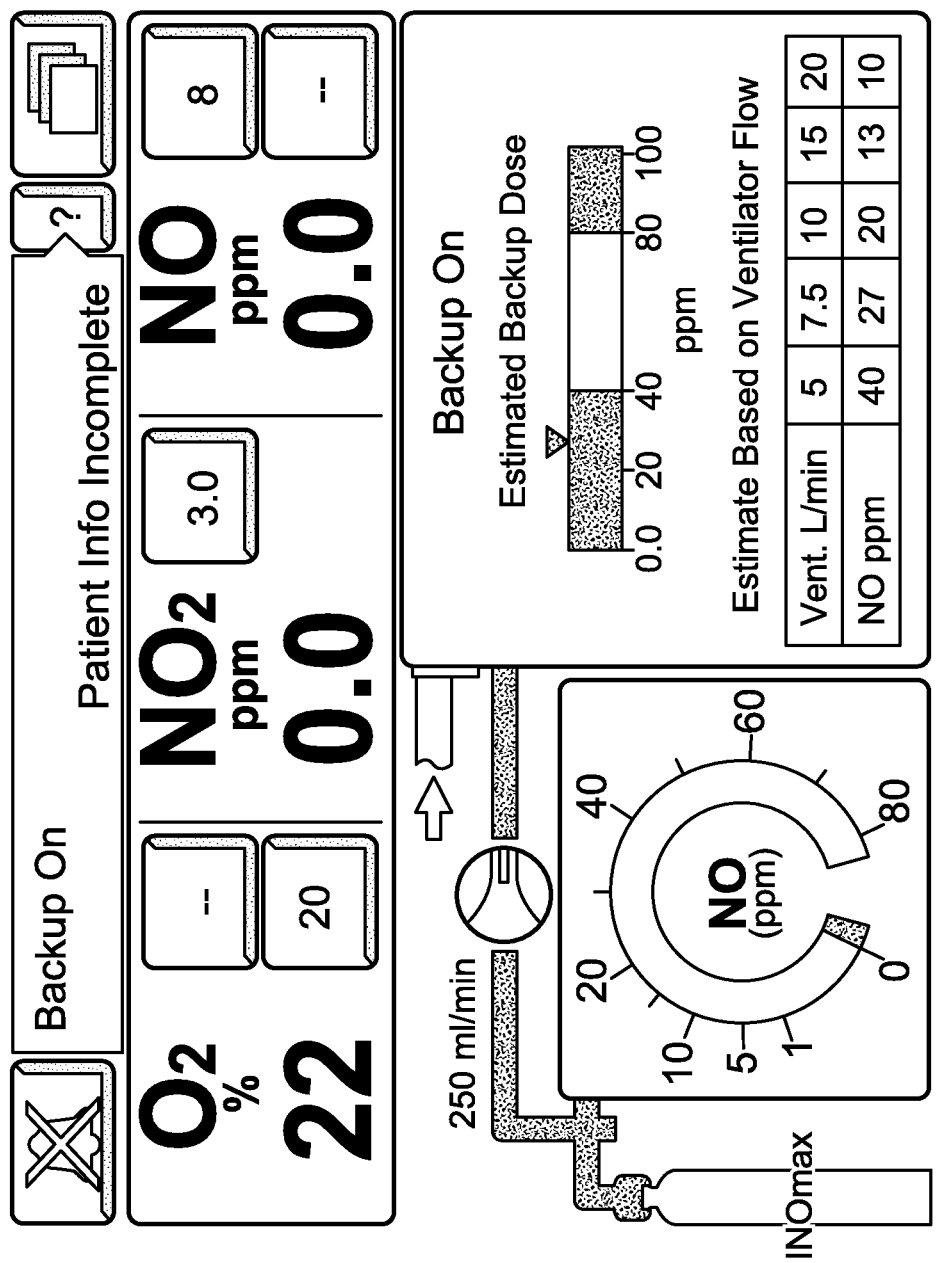
FIG. 7 depicts a screen displaying a calculated dose in ppm based on a known therapeutic gas flow rate and a measured breathing gas flow rate.

The CPU may also calculate a delivery concentration based on the measured nitric oxide flow rate and the measured flow rate through the breathing circuit. The calculated delivery concentration may be compared to the delivery concentration set by the user to provide a calculated delivery expressed as a percentage, with 100% being ideal delivery. In some embodiments, either the calculated delivery percentage and/or the calculated delivery concentration may be displayed on the screen as a calculated dose of nitric oxide. For example, the calculated delivery percentage may also be displayed on the screen as shown in FIG. 5, or the calculated delivery may be displayed as a NO concentration in ppm as shown in FIG. 7.

In FIG. 5, the calculated delivery indicator has a black target delivery region, a white over delivery region and a white under delivery region. The target delivery region may be based on a certain accuracy tolerance for nitric oxide delivery, such as +/−1%, +/−2%, +/−5%, +/−10%, +/−15%, +/−20%, +/−25%, +/−30%, +/−35%, +/−40%, +/−45%, +/−50%, +/−55%, +/−60%, +/−65%, +/−70%, +/−75%, +/−80%, +/−85%, +/−90%, +/−95% or +/−100%. If the calculated delivery is in the white over delivery region or the white under delivery region, an alarm may be emitted or other notification may be provided to the user. As with the displayed flow of breathing gas, the calculated delivery may be displayed as an instantaneous value, average value, minimum value and/or maximum value.

By providing an inspired flow graphic in combination with a % delivery error graphic, a user can ascertain the device NO proportional flow control limitations. With this information, a user can adjust the breathing gas flow rate and/or the desired ppm dose to ensure that the nitric oxide delivery system is not operating outside of its delivery range. With independent NO gas concentration monitoring one can further ascertain set verses measured deviation. Inadequate NO delivery could then be compensated by the user up or down from the desired set dose.

Figure 6:
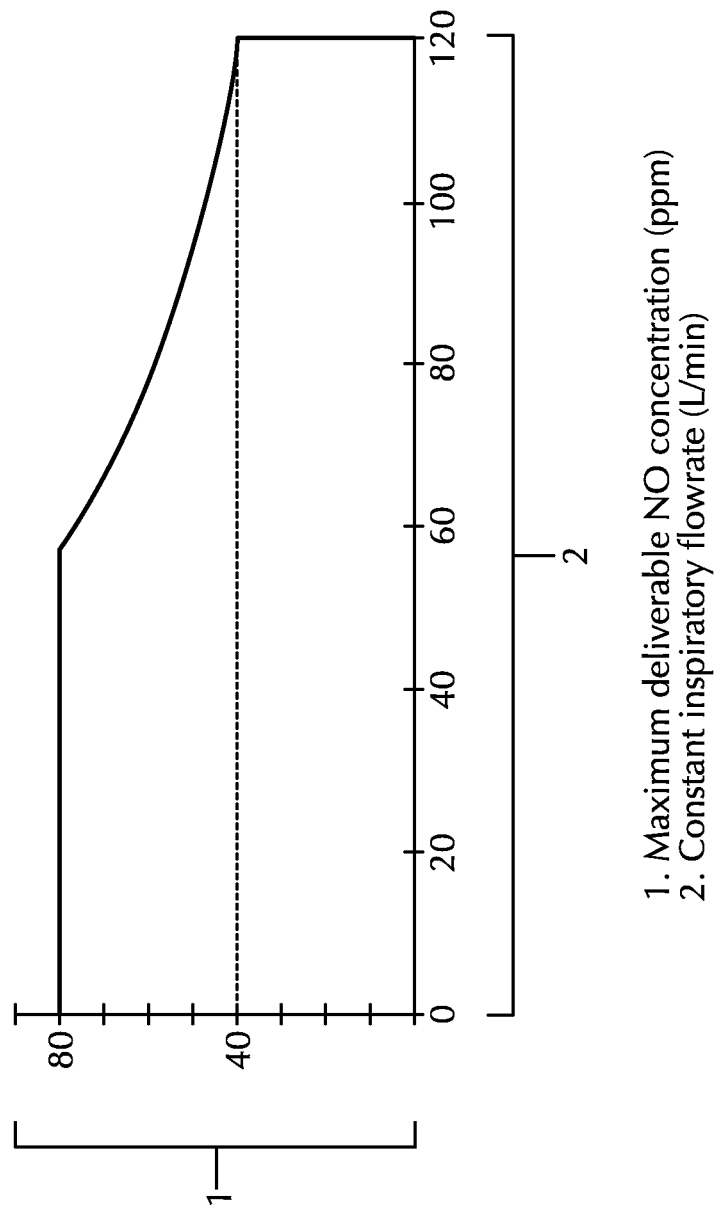
FIG. 6 depicts the maximum deliverable NO concentration as a function of the breathing gas flow rate for a nitric oxide delivery apparatus with a maximum NO flow rate.

Some current nitric oxide delivery systems have a maximum NO flow that can be delivered. For example, a nitric oxide delivery device may have a maximum NO flow of 6.35 L/min. This means the maximum deliverable NO concentration will vary based on the ventilator flow rate and the nitric oxide concentration in the therapeutic gas supply. For a cylinder having a NO concentration of 800 ppm, the maximum deliverable NO concentration will vary from approximately 80 ppm at a constant flow of 60 L/min to approximately 40 ppm at constant flow 120 L/min. FIG. 6 illustrates the NO delivery dose limitation for such a delivery system based on the expected ventilation inspired flow rates. For example, when inspired flows are sustained greater than 120 L/min with a dose set above 60 ppm, the potential exists for under-delivery shutdown conditions because the maximum NO flow rate cannot deliver the required NO to obtain the 60 ppm dose.

FIG. 7 shows an exemplary graphic for displaying the calculated dose of nitric oxide as a concentration in ppm. As can be seen, the calculated dose in ppm can be displayed as a graphic that indicates the concentration, but other ways of displaying the calculated dose can be displaying the calculated dose in ppm as an actual number, i.e. 26 ppm. Displaying the calculated dose as a concentration in ppm can be particularly useful if the nitric oxide delivery apparatus is in a backup mode in which the device does not provide proportional or ratio-metric delivery of nitric oxide. For example, in some situations it may be necessary to provide a constant flow of therapeutic gas that is independent of the breathing gas flow rate, such as a flow rate of 250 mL/min of therapeutic gas. In such a backup mode, the device may calculate the dose of nitric oxide based on the constant therapeutic gas flow rate and the measured breathing gas flow rate. The device may assume the constant therapeutic gas flow rate is a certain flow rate (i.e. 250 mL/min) or the constant therapeutic gas flow rate may actually be measured. As the flow of therapeutic gas is constant and is no longer dependent on the breathing gas flow rate, the concentration of nitric oxide delivered to the patient will vary depending on the breathing gas flow rate (i.e. the backup therapeutic gas delivery is non-ratio-metric to the measured breathing gas flow rate). Accordingly, it may be beneficial to provide an estimate of the backup dose based on the known therapeutic gas flow rate (which may be an assumed flow rate) and the measured breathing gas flow rate.

In a backup mode with a constant therapeutic gas flow rate, it may be useful to display a chart or other graphic on the display to help the clinician predict what the nitric oxide concentration will be for certain breathing gas flow rates. An example of such a chart is shown in the bottom right corner of FIG. 7. Using this information, the clinician may set the ventilator to a certain flow rate or pressure control to achieve the desired nitric oxide concentration for the backup mode delivery.

In some embodiments, the flow rate of breathing gas and/or the calculated nitric oxide dose is displayed on the main screen used during therapy. However, in one or more alternate embodiments, the flow rate and/or calculated dose is not directly displayed on the main screen, but the user may access a screen that displays information such as the breathing flow rate history or the instantaneous breathing gas flow rate. The breathing flow rate history may include the peak and/or average flow rates for a certain period of time, such as the past 5, 10, 15, 20, 30 or 45 seconds, the past 1, 2, 5, 10, 15, 20, 30, 45, 60 minutes, or since the start of the current therapy administration. In some embodiments, the breathing flow rate history is provided for the past several seconds, such as about 10 seconds. The apparatus may include appropriate components for calculating and storing the information regarding breathing flow rate history, such as a CPU and memory. Similarly, the calculated dose that is displayed may be instantaneous, average, maximum and/or minimum values. A calculated dose history may include the peak and/or average flow rates for a certain period of time, such as the past 5, 10, 15, 20, 30 or 45 seconds, the past 1, 2, 5, 10, 15, 20, 30, 45, 60 minutes, or since the start of the current therapy administration. In some embodiments, the calculated dose history is provided for the past several seconds, such as about 10 seconds.

The apparatus may comprise an input device that can receive input from a user. Such user input can include operation parameters, such as desired nitric oxide concentration and flow limits. In one embodiment, an input device and display device may be incorporated into one unit, such as a touchscreen device.

The breathing gas delivery system can include any system capable of providing a supply of breathing gas to the patient. The breathing gas may be supplied by ventilatory support, mechanically assisted ventilation or by spontaneous ventilation. Examples of suitable ventilation apparatuses include, but are not limited to, conventional ventilators, jet ventilators, high frequency oscillator ventilators and continuous positive airway pressure (CPAP) apparatuses. Non-invasive approaches can also be used to supply the breathing gas, including bubble CPAP, synchronized inspiratory positive airway pressure (SiPAP), nasal cannula and heated high flow nasal cannula.

The therapeutic injector module combines the flow of the breathing gas and the flow of the therapeutic gas. The injector module ensures the proper delivery of inhaled nitric oxide at a set dose based on changes in flow of the breathing gas via communication with the CPU.

In some embodiments, the nitric oxide delivery device is suitable for use with gentle ventilation strategies. Gentle ventilation may be a ventilator strategy that limits shear stress and pressures on the alveoli, while maintaining adequate oxygenation and ventilation, to reduce lung injury and minimize long term pulmonary complications. Gentle ventilation includes, but is not limited to: (1) maintaining adequate ventilation and oxygenation of the neonate; (2) limiting peak to peak pressures during mechanical ventilation; (3) adjusting ventilator pressure(s) as needed to maintain adequate lung volume without doing harm.

In some embodiments, gentle ventilation involves reducing inspiratory pressure enough to allow for some permissive hypercapnia. Gentle ventilation may include, but is not limited to, utilization of non-invasive ventilation (NIV) methods of respiratory support to limit injury to the lung, whereby the device and equipment supplies gas flow at lower pressures, thus eliminating the breath-to-breath high PIP's (Peak Inspiratory Pressures) which increases the frequency of lung injury through shearing forces and stretching of alveoli. Gentle ventilation may include the use of bubble CPAP, SiPAP, HHHFNC (Heated Humidified High Flow Nasal Cannula) and methods of mechanical ventilation, whereby the intubated infant receives PIP's less than or equal to 20 cm $H_2O$ and oxygen saturations are 88-92%. For those infants on HFOV or HJV, pressures are maintained to minimize lung injury. Equipment to maintain an approach to gentle ventilation includes, but is not limited to, nasal cannula, nasal prongs and adaptive masks for NIV support. Examples of suitable equipment for gentle ventilation are Neopuff® and High Flow Bubble CPAP available from Fisher & Paykel Healthcare, Inc., and products available from Vapotherm, Inc.

Another aspect of the invention relates to a system for delivering therapeutic gas to a patient. The system comprises: a therapeutic gas supply comprising nitric oxide; a breathing gas delivery system that provides breathing gas to a patient; and a therapeutic gas delivery apparatus, wherein the therapeutic gas delivery apparatus comprises: a first inlet configured to be placed in fluid communication with the therapeutic gas supply; a second inlet configured to be placed in fluid communication with the breathing gas delivery system; a therapeutic gas injector module adapted to be placed in communication with the first inlet and the second inlet to provide a combined flow of breathing gas and therapeutic gas; an outlet in fluid communication with the injector module and configured to supply breathing gas and therapeutic gas to a patient; a control circuit in communication with a first flow sensor that measures the flow of breathing gas from the breathing gas delivery system and a second flow sensor that measures the flow of therapeutic gas to determine a calculated dose of nitric oxide based on the therapeutic gas and breathing gas flow rates; and a display to provide a visual and/or numeric indication of the calculated dose of nitric oxide.

Figure 2:
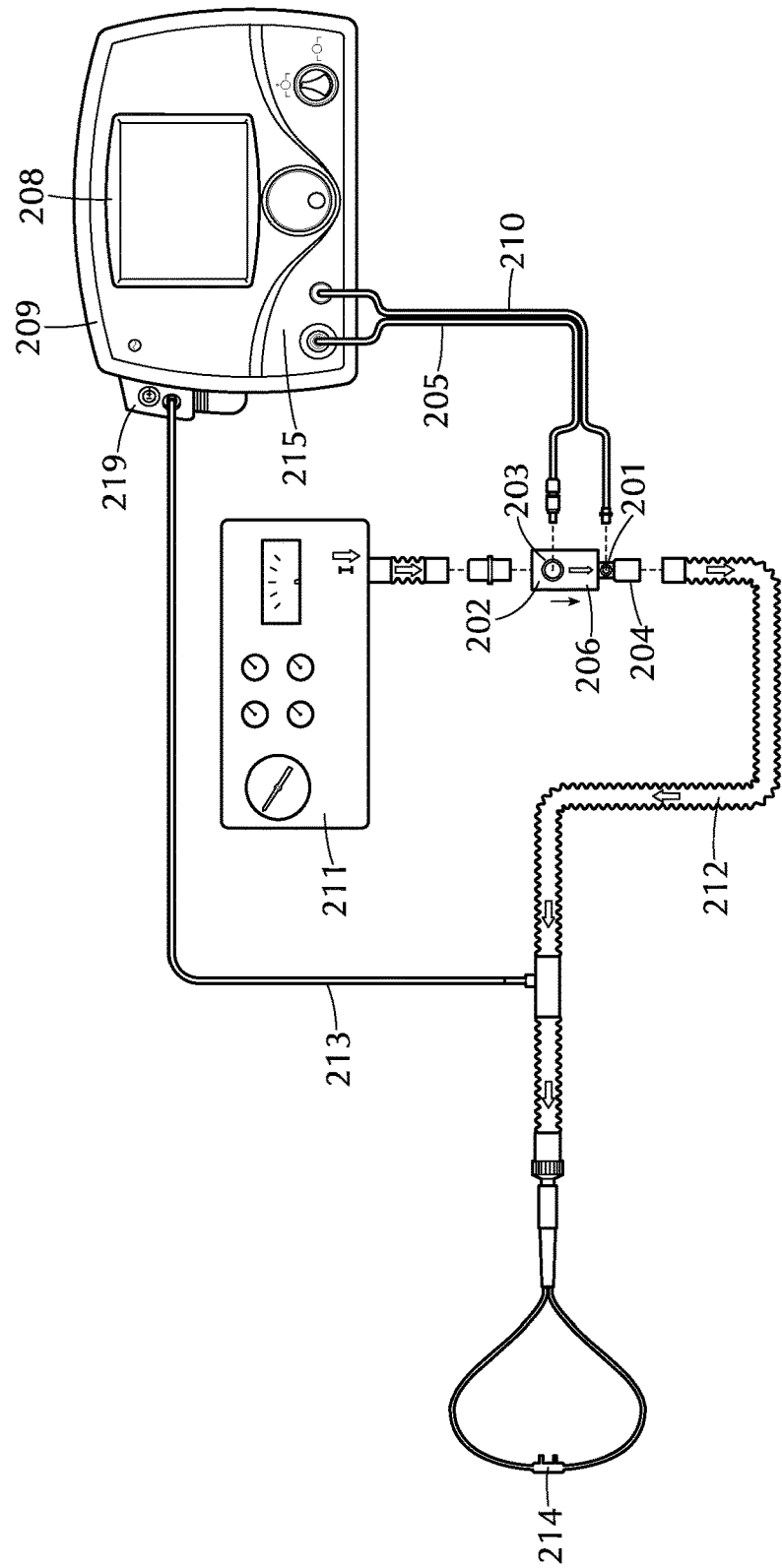
FIG. 2 depicts a system for providing a therapeutic gas to a patient in accordance with one or more embodiments of the invention.

FIG. 2 illustrates one embodiment of a system for providing a therapeutic gas to a patient in accordance with this aspect. Therapeutic injector module 203 is in fluid communication with first inlet 201 and second inlet 202. First inlet 201 is in fluid communication with therapeutic gas injector tube 210, which is in fluid communication with a therapeutic gas supply comprising nitric oxide. Second inlet 202 is in fluid communication with breathing gas delivery system 211, which is illustrated as a ventilator. The arrows in FIG. 2 indicate the direction of flow for the breathing gas and the combined gas mixture of therapeutic gas and breathing gas. Flow sensor 206 is in fluid communication and downstream of second inlet 202, and monitors the flow of breathing gas through therapeutic injector module 203. The top view of therapeutic injector module 203 is shown. The therapeutic gas and breathing gas mix in therapeutic injector module 203 to provide a gas mixture. Injector module cable 205 connects therapeutic injector module 203 with control module 209. Flow sensor 206 in the control module 209 measures the flow of therapeutic gas flowing through therapeutic gas injector tube 210 to the therapeutic injector module 203. Control module 209 also comprises display 208, which can display real-time flow of breathing gas and/or calculated dose of nitric oxide and/or provide alerts when the flow of breathing gas rises above or falls below a predetermined level. Inspiratory breathing hose 212 is in fluid communication with outlet 204 and nasal cannula 214. The inspiratory breathing hose provides the gas mixture of breathing gas and therapeutic gas to nasal cannula 214, which delivers the gas mixture to the patient. Patient gas sample line 213 diverts some of the flow of the gas mixture from inspiratory breathing hose 212 and brings it to sample block 219.

Sample block 219, also known as a sample pump, draws some of the flow of the gas mixture through gas sample line 213. As shown in FIG. 2, the sample block 219 may be incorporated into the control module 209. The sample block analyzes the concentrations of nitric oxide, oxygen, and nitrogen dioxide in the gas mixture. Typically, a sample block will sample about 250 mL/min of the gas mixture. However, when flow rates of breathing gas are near 250 mL/min, sampling 250 mL/min of the gas mixture would leave little or no gas to deliver to the patient. Therefore, in one or more embodiments, the sample block is modified to draw or pull a volume of combined therapeutic and breathing gas such that the gas sampled per minute is less than or equal to 100 mL/min. In certain embodiments, the gas sampled is less than or equal to 50 mL/min. In further embodiments, the gas sampled is less than or equal to 20 mL/min. The sampling block may have smaller pumps or more sensitive sensors in order to sample lower flow rates.

The concentrations of nitric oxide, oxygen and nitrogen dioxide measured in the sample block 219 may be shown on display 208. As a result of sampling lower amounts of the gas mixture, refresh rates of monitored values may need to be faster regarding displayed values.

The therapeutic gas delivery apparatus in the therapeutic gas delivery system can incorporate any or all of the previously described embodiments for a therapeutic gas delivery apparatus.

The breathing gas delivery system in the system for delivering therapeutic gas can include any system capable of providing a supply of breathing gas to the patient. The breathing gas may be supplied by any form of ventilatory support, or mechanically assisted ventilation or by spontaneous ventilation. Examples of suitable ventilation apparatuses include, but are not limited to, conventional ventilators, jet ventilators, high frequency oscillator ventilators and CPAP apparatuses. Non-invasive approaches can also be used to supply the breathing gas, including bubble CPAP, SiPAP, nasal cannula and heated high flow nasal cannula.

According to another aspect of the invention, provided is a method of monitoring the delivery of therapeutic gas to a patient comprising: providing a flow of breathing gas; providing a flow of therapeutic gas comprising nitric oxide; measuring the flow of breathing gas; measuring the flow of therapeutic gas; delivering the breathing gas and therapeutic gas to a patient; determining a calculated dose of nitric oxide based on the measured flow of breathing gas and the measured flow of therapeutic gas or a known flow of therapeutic gas; and displaying the calculated dose of nitric oxide on a display module.

Figure 3:
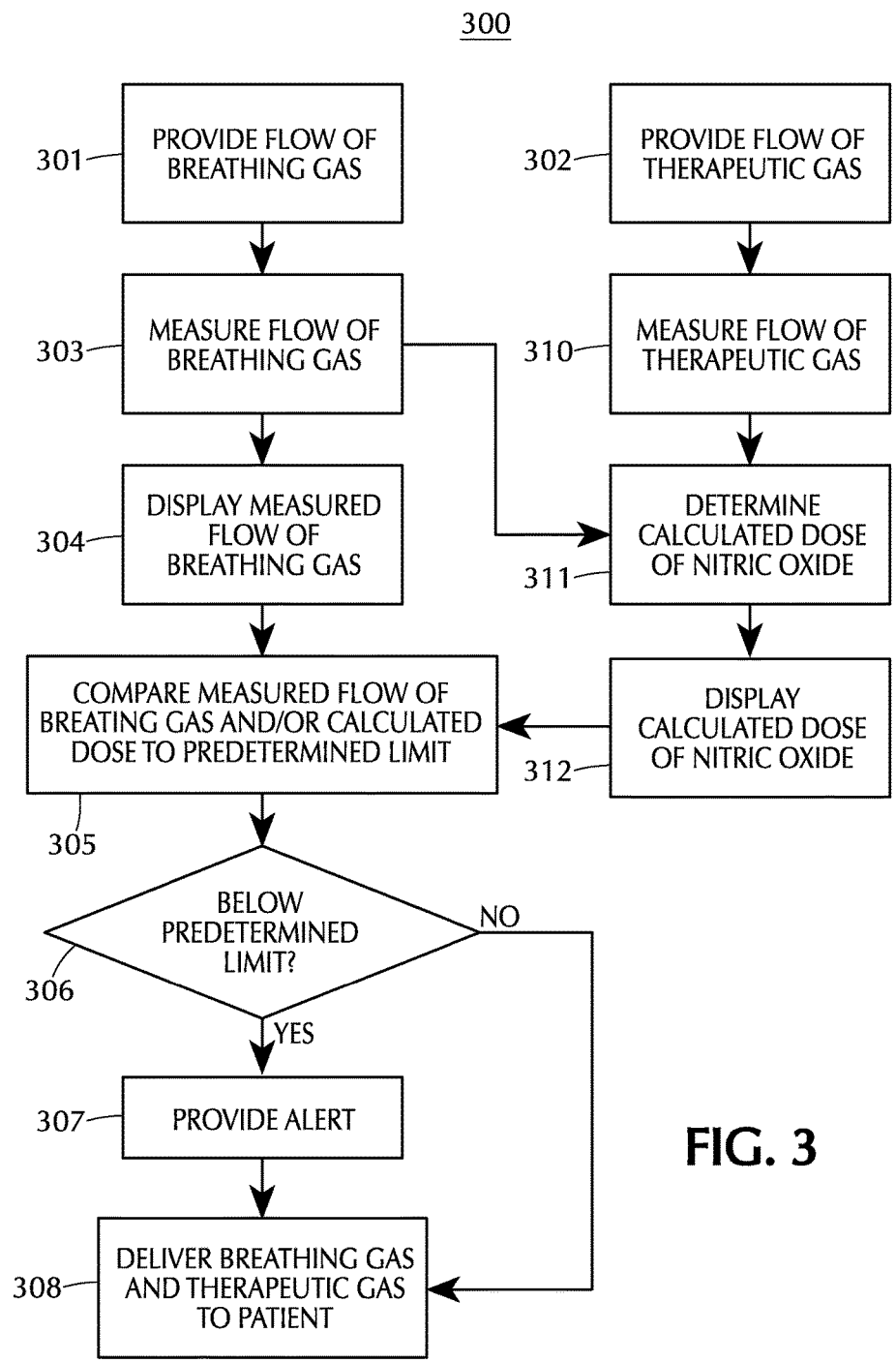
FIG. 3 depicts a flow chart for a method of monitoring the delivery of therapeutic gas to a patient in accordance with one or more embodiments of the invention.

FIG. 3 depicts a flow chart for one embodiment of a method 300 for monitoring the delivery of therapeutic gas to a patient. A flow of breathing gas is provided 301 to a delivery apparatus, such as a therapeutic injector module. The flow of breathing gas may be provided from a ventilator to an injector module as described above. A flow of therapeutic gas comprising nitric oxide is also provided 302 to the delivery apparatus. The flow of breathing gas is measured 303, and this measured flow of breathing gas may be displayed 304 on a display module. The flow of therapeutic gas is also measured 310. The measured flow rates of breathing gas and therapeutic gases are then used to determine a calculated dose of nitric oxide 311, and then the calculated dose of nitric oxide may be displayed 312. Instead of using a measured flow rate of therapeutic gas, a known flow rate of therapeutic gas may be used. The measured flow of breathing gas and/or the calculated dose of nitric oxide may be compared 305 to a predetermined limit. In FIG. 3, the predetermined limit is a low limit. If the measured flow of breathing gas and/or calculated dose is below 306 the predetermined limit, an alert is provided 307. The breathing gas and therapeutic gas are then delivered 308 to a patient. For example, the injector module may combine the flow of breathing gas from the ventilator with the flow of therapeutic gas from the nitric oxide delivery device and provide this combined flow to the patient. If the measured flow of breathing gas and/or calculated dose is not below 306 the predetermined limit, then the breathing gas and therapeutic gas are delivered 308 to a patient without providing 307 an alert. Any of the steps provided above are optional, and the scope of any particular method is not limited by the specific combination shown in FIG. 3.

Figure 4:
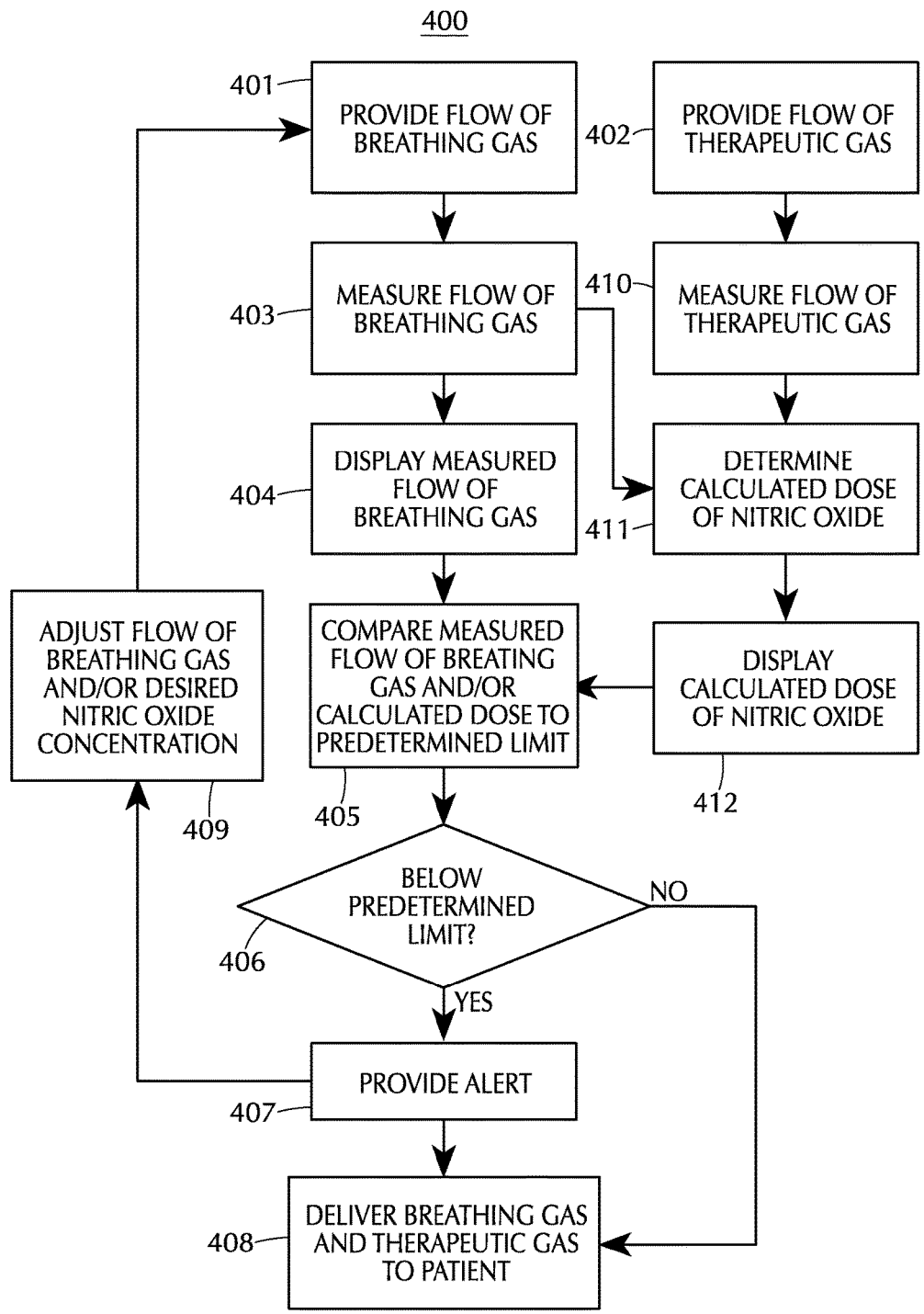
FIG. 4 depicts a flow chart for another method of monitoring the delivery of therapeutic gas with a feedback loop to drive NO dose or adjust flows to a patient in accordance with one or more embodiments of the invention.

FIG. 4 depicts a flow chart for another embodiment of a method 400 for monitoring the delivery of therapeutic gas to a patient. A flow of breathing gas is provided 401 to a delivery apparatus, and a flow of therapeutic gas comprising nitric oxide is also provided 402. The flow of breathing gas is measured 403, and the measured flow of breathing gas may be displayed 404 on a display module. The flow of therapeutic gas is also measured 410. The measured flow rates of breathing gas and therapeutic gases are then used to determine a calculated dose of nitric oxide 411, and then the calculated dose of nitric oxide may be displayed 412. The measured flow of breathing gas and/or the calculated dose of nitric oxide may be compared 405 to a predetermined limit, which is a low limit in FIG. 4. As with FIG. 3, if the measured flow of breathing gas and/or the calculated dose is below 406 the predetermined limit, an alert is provided 407. In response to the alert provided 407, the flow rate of breathing gas and/or the desired nitric oxide concentration may be adjusted 409. The breathing gas and therapeutic gas comprising nitric oxide are then delivered 408 to the patient. If the measured flow of breathing gas and/or calculated dose is not below 406 the predetermined limit, then proceed directly to delivering 408 the breathing gas and therapeutic gas comprising nitric oxide. Again, any of the steps provided above are optional, and the scope of any particular method is not limited by the specific combination shown in FIG. 4.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

What is claimed is:

1. An apparatus to deliver therapeutic gas to a patient, the apparatus comprising:
   a first inlet to be placed in fluid communication with a therapeutic gas supply providing a continuous flow of nitric oxide at a therapeutic gas supply concentration;
   a second inlet to be placed in fluid communication with a breathing gas delivery system providing a continuous flow of a breathing gas to the patient;
   a therapeutic gas injector module to be placed in fluid communication with the first inlet and the second inlet to provide a combined continuous flow of breathing gas and therapeutic gas;
   an outlet in fluid communication with the therapeutic gas injector module to supply the combined continuous flow of breathing gas and therapeutic gas to the patient;
   a control circuit including a first flow sensor to measure the continuous flow of breathing gas from the breathing gas delivery system and a second flow sensor to measure the continuous flow of therapeutic gas, wherein the control circuit determines a calculated dose of nitric oxide based on the measured flow of breathing gas and either the measured flow of therapeutic gas or a known continuous flow of therapeutic gas; and
   a display in communication with the control circuit that provides a visual and/or numeric indication of the calculated dose of nitric oxide, wherein the visual and/or numeric indication of the calculated dose of nitric oxide is provided as a percentage of a desired delivery concentration to be delivered to the patient, wherein the desired delivery concentration is set by a user; and
   wherein the visual and/or numeric indication of the calculated dose of nitric oxide as the percentage of the desired delivery concentration is indicated on the display as being in one of a target delivery region, an under-delivery of nitric oxide region, and an over-delivery of nitric oxide region.

2. The apparatus of claim 1, wherein the calculated dose of nitric oxide is one or more of an average calculated dose, an instantaneous calculated dose, a maximum calculated dose and/or a minimum calculated dose.

3. The apparatus of claim 1, further comprising an indicator that provides an alert when the flow of breathing gas or calculated dose of nitric oxide rises above or falls below a predetermined level.

4. The apparatus of claim 3, wherein the alert includes one or more of an audible alert, a visual alert and/or a text alert.

5. The apparatus of claim 3, wherein the indicator is an icon or graphic on the display that provides a visual and/or numeric indication of the measured flow of breathing gas.

6. The apparatus of claim 1, wherein the display also provides a visual and/or numeric indication of the measured flow of breathing gas.

7. The apparatus of claim 6, wherein the visual and/or numeric indication of the measured flow of breathing gas includes one or more of volumetric flow rate, tidal volume, and/or minute ventilation.

8. The apparatus of claim 6, wherein the measured flow of breathing gas is one or more of an average flow rate, an instantaneous flow rate, a peak flow rate and/or a minimum measured flow rate.

9. The apparatus of claim 1, wherein the breathing gas delivery system comprises a ventilation apparatus.

10. The apparatus of claim 1, wherein the control circuit further comprises clinical decision support software to reset any upper and lower limits of maximum and minimum calculated dose to avert shutdown of the apparatus.

11. The apparatus of claim 1, wherein the display further provides a chart that provides a predicted nitric oxide concentration as a function of the measured flow of breathing gas.

12. A method of monitoring the delivery of therapeutic gas to a patient comprising:
providing a continuous flow of breathing gas;
providing a continuous flow of therapeutic gas comprising nitric oxide;
measuring the continuous flow of breathing gas to obtain a measured flow of breathing gas; measuring the continuous flow of therapeutic gas comprising nitric oxide to obtain a measured flow of therapeutic gas or obtaining a known continuous flow of therapeutic gas;
receiving from a user a desired delivery concentration of the therapeutic gas to be delivered to the patient;
delivering the breathing gas and therapeutic gas to the patient;
determining a calculated dose of nitric oxide based on the measured flow of breathing gas and either the measured flow of therapeutic gas or the known continuous flow of therapeutic gas; and
displaying a visual and/or numeric indication of the calculated dose of nitric oxide on a display module, wherein the calculated dose of nitric oxide is provided as a percentage of the desired delivery concentration;
wherein the visual and/or numeric indication of the calculated dose of nitric oxide as the percentage of the desired delivery concentration is indicated on the display as being in one of a target delivery region, an under-delivery of nitric oxide region, and an over-delivery of nitric oxide region.

13. The method of claim 12, further comprising comparing the calculated dose of nitric oxide to a predetermined limit and providing an alert if the calculated dose of nitric oxide is above or below the predetermined limit.

14. The method of claim 13, wherein the alert includes one or more of an audible alert, a visual alert and/or a text alert.

15. The method of claim 13, wherein the predetermined limit comprises a delivery error greater than or equal to about 25%.

16. The method of claim 12, wherein the calculated dose of nitric oxide is one or more of an average calculated dose, an instantaneous calculated dose, a maximum calculated dose and/or a minimum calculated dose.

17. The method of claim 12, further comprising displaying the measured flow of breathing gas.

18. The method of claim 17, wherein displaying the measured flow of breathing gas includes displaying one or more of volumetric flow rate, tidal volume, and/or minute ventilation.

19. The method of claim 17, wherein the measured flow of breathing gas is one or more of an average flow rate, an instantaneous flow rate, a peak flow rate and/or a minimum measured flow rate.

* * * * *